United States Patent [19]

Dockner et al.

[11] Patent Number: 5,663,421

[45] Date of Patent: Sep. 2, 1997

[54] SEPARATION OF A DIESTER OF (METH) ACRYLIC ACID WITH A $C_4$–$C_6$-ALKANEDIOL

[75] Inventors: Toni Dockner, Meckenheim; Helmut Lermer, Ludwigshafen; Ulrich Rauh, Limburgerhof; Gerhard Nestler, Ludwigshafen, all of Germany

[73] Assignee: BASF Aktiengesellschaft, Ludwigshafen, Germany

[21] Appl. No.: 541,703

[22] Filed: Oct. 10, 1995

[30] Foreign Application Priority Data

Oct. 11, 1994 [DE] Germany ............ 44 36 242.0

[51] Int. Cl.⁶ ............................................ C07C 67/48
[52] U.S. Cl. ............................................ 560/218
[58] Field of Search .................................. 560/218

[56] References Cited

FOREIGN PATENT DOCUMENTS

| 0 465 853 | 1/1992 | European Pat. Off. . |
| 1 518 572 | 1/1969 | Germany . |
| 42 28 397 | 3/1994 | Germany . |

OTHER PUBLICATIONS

Ullmann's Encyclopedia, vol. 19, No. 4, pp. 10–30, 1980, "Polyacryl–und Polymethacryl–Verbindungen".

Roempp Chemie Lexicon, pp. 528–529, 1989, "Butandiole".

Ullmann's Encyclopedia, vol. 19, pp.9–14, 1980, "Parkinsonism Treatment".

Technische Information, Edition 1331 d, 2 pages, Jun. 1995, "Butandiolmonoacrylat".

*Primary Examiner*—Paul J. Killos
*Attorney, Agent, or Firm*—Oblon, Spivak, McClelland, Maier & Neustadt, P.C.

[57] ABSTRACT

A diester of (meth)acrylic acid with a $C_4$–$C_6$-alkanediol is separated from a mixture which essentially consists of the $C_4$–$C_6$-alkanediol, the monoester of (meth)acrylic acid with the $C_4$–$C_6$-alkanediol and the diester of (meth)acrylic acid with the $C_4$–$C_6$-alkanediol by extraction with an organic solvent in the presence of water, by a process in which the diester-containing mixture is added continuously in the middle section of an extraction column and in addition water and the organic extracting agent are passed continuously countercurrent in the extraction column.

11 Claims, No Drawings

SEPARATION OF A DIESTER OF (METH) ACRYLIC ACID WITH A $C_4$–$C_6$-ALKANEDIOL

The present invention relates to a process for separating a diester of (meth)acrylic acid with a $C_4$–$C_6$-alkanediol from a mixture which consists essentially of the $C_4$–$C_6$-alkanediol, the monoester of (meth)acrylic acid with the $C_4$–$C_6$-alkanediol and the diester of (meth)acrylic acid with the $C_4$–$C_6$-alkanediol by extraction with an organic solvent in the presence of water.

(Meth)acrylic acid is used as an abbreviation for acrylic acid or methacrylic acid.

Diesters of (meth)acrylic acid with a $C_4$–$C_6$-alkanediol form un-avoidable by-products in the preparation of monoesters of (meth)acrylic acid with $C_4$–$C_6$-alkanediols by direct esterification of (meth)acrylic acid with the corresponding alkanediols. Both the monoesters of (meth)acrylic acid with $C_4$–$C_6$-alkanediols and the diesters of (meth)acrylic acid with $C_4$–$C_6$-alkanediols are interesting starting compounds owing to their bifunctionality.

For example, the monoesters of (meth)acrylic acid with $C_4$–$C_6$-alkanediols are suitable as vinylically unsaturated comonomers in polymers which are produced by free radical polymerization and are suitable, for example, as binders. As alcoholic compounds, however, they are also suitable, for example, for polymeranalogous reactions (for example condensation or addition reactions). Diesters of (meth)acrylic acid with $C_4$–$C_6$-alkanediols are also suitable as divinylically unsaturated compounds, for example as comonomers of polymers dispersed in an aqueous medium, in order to crosslink said polymers. Regarding the abovementioned intended uses, it is necessary that both the monoesters of (meth)acrylic acid with $C_4$–$C_6$-alkanediols and the diesters of (meth)acrylic acid with $C_4$–$C_6$-alkanediols are available in high purity. Both monoesters of (meth)acrylic acid with $C_4$–$C_6$-alkanediols and the diesters of (meth)acrylic acid with $C_4$–$C_6$-alkanediols are characterized in Ullmanns Encyclopädie der technischen Chemie, Polyacryl-Verbindungen, Vol. 19, 4th Edition, Verlag Chemie (1980), page 10.

The preparation of monoesters of (meth)acrylic acid with $C_4$–$C_6$-alkanediols by direct esterification of (meth)acrylic acid with the corresponding alkanediols in the presence of acidic esterification catalysts and with removal of the resulting water by azeotropic distillation with a suitable entraining agent is disclosed, for example, in German Patent 1,518,572 and EP-A 465 853.

Since alcohols generally tend to undergo secondary reactions, such as ether formation, under the influence of the acidic esterification catalysts, the esterification is preferably carried out only with a small excess of the alkanediol. Under such conditions, considerable amounts of the corresponding diesters are usually formed, so that the product mixture generally obtained is one which consists essentially of entraining agent,
alkanediol,
monoester and
diester and from which the desired monoester has to be separated. The fact that the alkanediol, monoester and diester have high boiling points even under reduced pressure,
the boiling points of alkanediol, monoester and diester are very close together and
the vinylically unsaturated monoesters and diesters have a greater tendency to polymerization, especially in the condensed phase and at elevated temperatures, is disadvantageous for the required separation.

In the case of acrylic acid as the starting acid and 1,4-butanediol as the alkanediol, the relevant boiling points at atmospheric pressure (1 atm) are, for example:

1,4-butanediol: 230° C. (Römpp Chemie Lexikon, 9th Edition, Thieme Verlag, Stuttgart, 1989);

1,4-butanediol monoacrylate: about 230° C. (Technical Information TI/ED 1331 d from 1987, BASF Aktiengesellschaft);

1,4-butanediol diacrylate: about 225° C. (Ullmanns Encyklopädie der technischen Chemie, Vol. 19, Verlag Chemie, Weinheim, 1980, page 9).

Under these conditions, separation by rectification is in fact impossible for economic reasons (cf. also German Laid-Open Application DOS 4,228,397).

For the separation of the product mixture, German Patent 1,518,572 recommends adding water to said mixture and first extracting the diester with an extracting agent in the presence of the aqueous phase. The extracting agent usually used is one which is simultaneously suitable as an entraining agent for the esterification, in order to be able to recycle the diester-containing organic extraction phase directly to the esterification. Otherwise, the entraining agent would have to be separated off, for example by distillation, before the extraction of the diester. If required, it is of course also possible to isolate the diester from the organic extraction phase (for example removal of the extracting agent by distillation). The presence of the aqueous phase is required in order to prevent the organic extraction phase also from taking up significant amounts of monoester. The latter is thus obtained as a component of the aqueous phase and can be recovered from said phase in a subsequent further extraction step.

The disadvantage of German Patent 1,518,572 is that it recommends first diluting the mixture containing alkanediol, monoester and diester with water and then passing the resulting aqueous mixture countercurrent to the extracting agent in an extraction column. The amount of water required in this procedure is stated as being five times (5 times) the amount of the mixture to be separated.

EP-A 465 853 recommends carrying out the esterification in the presence of considerable amounts of added preformed diester in order thus to minimize the amount of unconverted alkanediol in the product mixture. Furthermore, EP-A 465 853 recommends washing out the catalytic acid from the product mixture and then directly extracting the diester compound in the absence of water with appropriate extracting agents, as also recommended in German Patent 1,518, 572. However, the disadvantage of this procedure is that considerable amounts of monoester thus pass over into the extracting agent and subsequently have to be washed out of said extracting agent with water in a second step.

It is an object of the present invention to provide a process for separating a diester of (meth)acrylic acid with a $C_4$–$C_6$-alkanediol from a mixture which essentially consists of the $C_4$–$C_6$-alkanediol, the monoester of (meth)acrylic acid with the $C_4$–$C_6$-alkanediol and the diester of (meth)acrylic acid with the $C_4$–$C_6$-alkanediol by extraction with an organic solvent in the presence of water, which process ensures completely satisfactory sharpness of separation between the diester of (meth)acrylic acid and the monoester of (meth) acrylic acid and the alkanediol even when a reduced amount of water is used.

We have found that this object is achieved by a process for separating a diester of (meth)acrylic acid with a $C_4$–$C_6$-alkanediol from a mixture which essentially consists of the $C_4$–$C_6$-alkanediol, the monoester of (meth)acrylic acid with the $C_4$–$C_6$-alkanediol and the diester of (meth)acrylic acid with the $C_4$–$C_6$-alkanediol by extraction with an organic solvent in the presence of water, wherein the diester-containing mixture is added continuously in the middle section of an extraction column and in addition water and the organic extracting agent are passed continuously countercurrent in the extraction column. Usually, water has a higher specific gravity than the extracting agent and is therefore taken up at the top of the column while the extracting agent having a lower specific gravity is pumped into the lower end of the extraction column. Under the abovementioned conditions, the organic phase containing the diester of (meth)acrylic acid with the $C_4$–$C_6$-alkanediol (the extract) can be taken off continuously at the top of the column while the aqueous phase containing the alkanediol and the monoester (the raffinate) can be taken off continuously at the bottom of the column.

Suitable extraction columns are in principle all those which are also useful for countercurrent distillation processes, ie. plate columns, packed columns and rotary columns (stirred stills, rotary-disk extractors and whirl columns). Packed columns are preferably used, among which in turn those which contain Pall rings as Raschig rings as packing are preferred. The packings are present as a rule on a support grid, and the liquid phases are generally distributed over the cross-section of the column by means of nozzle tubes. The phase having the lower specific gravity ascends in the phase having the higher specific gravity. The extraction column may be operated with or without pulsation.

Here, the middle section of the extraction column is understood as meaning the section which, when considered from the middle of the extractive section (of the extractive total zone) of the extraction column, includes 50% of the extractive upper section and 50% of the extractive lower section of the extraction column.

Advantageously used extracting agents are aliphatic or cycloaliphatic hydrocarbons having boiling points of from 65° to 120° C. at atmospheric pressure (1 atm). Examples of these are pentanes, cyclpentane, hexanes, cyclohexane, heptanes, cycloheptane, methylcyclohexane and octanes. As a rule, the extraction column has from 2 to 10, preferably from 4 to 6, theoretical plates.

The novel process is usually carried out at atmospheric pressure (1 atm) and at an extraction temperature of from 10° to 60° C., preferably from 20° to 40° C.

The novel process is advantageously used when the (meth)acrylic diester to be separated off is the diester of acrylic acid with 1,4-butanediol or 1,6-hexanediol, which is to be separated from the corresponding acrylic monoester in the mixture with the corresponding alkanediol.

The novel process is particularly advantageously used when the extraction material is obtained as the product mixture of a classical esterification of (meth)acrylic acid with a $C_4$–$C_6$-alkanediol in the presence of acidic esterification catalysts and with removal of the resulting water by azeotropic distillation with one of the abovementioned advantageous extracting agents as entraining agent.

An initial molar ratio of (meth)acrylic acid to alkanediol of from 1:1 to 1:3 is advantageously chosen for the esterification. Particularly suitable alkanediols are 1,6-hexanediol and 1,4-butanediol. The esterification catalysts used are as a rule acids such as p-toluenesulfonic acid, sulfuric acid, methanesulfonic acid and phosphoric acid. Usually, from 0.1 to 3% by weight, based on the acid to be esterified, of acidic catalyst are used. The esterification temperature is advantageously from 80° to 140° C. The esterification can be carried out under reduced or superatmospheric pressure. However, atmospheric pressure (1 atm) is usual. The esterification is advantageously carried out continuously in a cascade of from 2 to 4 reaction vessels, of which the first vessel is connected to feed lines while only the water of reaction and finally the product mixture are removed from the following vessels. A preferred entraining agent for the water to be removed is cyclohexane. It is simultaneously the agent preferably used for extracting the diester. The amount of the entraining agent is advantageousy such that the discharged reaction mixture from the final vessel of the cascade contains from 20 to 40% by weight of entraining agent. The diester-containing extract separated off in the novel extraction is advantageously recycled to the esterification cascade and distributed over the various reaction vessels in accordance with the amount of water to be removed from the particular vessel.

The novel process can therefore advantageously be used if the extraction mixture consists of from 5 to 20% by weight of the diester of (meth)acrylic acid with a $C_4$–$C_6$-alkanediol, from 20 to 40% by weight of the monoester of (meth)acryiic acid with a $C_4$–$C_6$-alkanediol, from 15 to 25% by weight of the $C_4$–$C_6$-alkanediol, from 20 to 50% by weight of an extracting agent and $\leq 5\%$ by weight of other compounds (for example (meth)acrylic acid, catalytic acid, water, polymerization inhibitor, by-products).

This is particularly true when the mixture is the product mixture from the esterification of acrylic acid with 1,4-butanediol or 1,6-hexanediol.

In the novel process, the extracting agent, extraction material and water are fed to the extraction column in amounts by weight such that the following is true:

Weight of added water/weight of added extraction material=from 2 to 4, preferably from 2 to 3;

Weight of added extracting agent/weight of added extraction material=from 1 to 4, preferably from 2 to 3.

Remarkably, the novel process achieves a completely satisfactory sharpness of separation between diester and monoester. It is furthermore surprising that there are no phase separation problems at all in the novel process.

The extraction column to be used according to the invention is preferably a pulsed column, ie. the phase having a lower specific gravity is forced into the lower end of the extraction column in a pulsating manner by means of a pulsation pump.

In the novel process, an extract which contains less than 0.1% by weight of the monoester of (meth)acrylic acid with the $C_4$–$C_6$-alkanediol is generally obtained, ie. the monoester of (meth)acrylic acid with the $C_4$–$C_6$-alkanediol as well as the alkanediol itself are present virtually exclusively in the aqueous phase.

The monoester of (meth)acrylic acid with the $C_4$–$C_6$-alkanediol can be separated off from said aqueous phase by extraction, for example by subsequent extraction (methylene chloride, an ester of a $C_1$–$C_4$-alkanecarboxylic acid and a $C_1$–$C_5$-alkanediol or a simple or mixed dialkyl ether of 4 to 8 carbon atoms. By using subsequent distillative operations, the pure monoester of (meth)acrylic acid with the $C_4$–$C_6$-alkanediol is obtained. Remarkably, the novel extraction of the (meth)acrylic diester is more selective if the product mixture from the preparation of the (meth)acrylic monoester is neutralized only after the diester has been separated off. Of course, the novel process step, as in the case of all other process steps along the route to the monoester of (meth)acrylic acid with a $C_4$–$C_6$-alkanediol is carried out in the presence of conventional amounts of the usual polymerization inhibitors. This was also the case in the example below. Particularly advantageous polymerization inhibitors to be used for this purpose are phenothiazine, hydroquinone and hydroquinone monomethyl ether.

EXAMPLE

A pulsed packed column filled with Raschig rings and having four (4) theoretical plates was fed, in the middle section, with 1400 kg/hour of the following mixture which was obtained in a classicial esterification of acrylic acid with 1,4-butanediol for the preparation of the monoester of 1,4-butanediol monoacrylate:

13% by weight of 1,4-butanediol diacrylate,

29% by weight of 1,4-butanediol monoacrylate,

19% by weight of 1,4-butanediol,

35% by weight of cyclohexane and

5% by weight of other compounds.

3600 kg/hour of water were added at the top of the column. 3300 kg/hour of cyclohexane were fed in at the bottom of the column via a pulsation pump.

The extraction temperature was 25° C.

The extract removed comprised 4000 kg/hour of a cyclohexane phase which contained 4.5% by weight of 1,4-butanediol diacrylate and 0.05% by weight of 1,4-butanediol monoacrylate.

The raffinate removed comprised 4300 kg/hour of an aqueous phase which contained 6.2% by weight of 1,4-butanediol, 8.9% by weight of 1,4-butanediol monoacrylate and 0.04% by weight of 1,4-butanediol diacrylate.

We claim:

1. A process for separating a diester of (meth)acrylic acid with a $C_4$–$C_6$-alkanediol from a mixture which essentially consists of the $C_4$–$C_6$-alkanediol, the monoester of (meth)acrylic acid with the $C_4$–$C_6$-alkanediol and the diester of (meth)acrylic acid with the $C_4$–$C_6$-alkanediol by extraction with an organic solvent in the presence of water, wherein the diester-containing mixture is added continuously in the middle section of an extraction column and in addition water and the organic solvent are passed continuously countercurrent in the extraction column.

2. A process as claimed in claim 1, wherein the extracting agent used is an aliphatic or cycloaliphatic hydrocarbon whose boiling point is from 65° to 120° C. at 1 atm.

3. A process as claimed in claim 1, wherein the extracting agent used is cyclohexane.

4. A process as claimed in claims 1, wherein the extraction material consists of from 5 to 20% by weight of the diester of (meth)acrylic acid with a $C_4$–$C_6$-alkanediol, from 20 to 40% by weight of the monoester of (meth)acrylic acid with a $C_4$–$C_6$-alkanediol, from 15 to 25% by weight of the $C_4$–$C_6$-alkanediol, from 20 to 50% by weight of the extracting agent and $\leq 5\%$ by weight of other compounds.

5. A process as claimed in claim 1, wherein the (meth)acrylic diester to be separated off is the diester of acrylic acid with 1,4-butanediol or 1,6-hexanediol, which is to be separated off from the corresponding acrylic monoester in the mixture with the corresponding alkanediol.

6. A process as claimed in claim 1, wherein the extracting agent, extraction material and water are fed to the extraction column in amounts by weight such that the following is true:

weight of added water/weight of added extraction material=from 2 to 4 and weight of added extracting agent/weight of added extraction material=from 1 to 4.

7. A process as claimed in claim 1, wherein the extraction temperature is from 20° to 40° C.

8. A process as claimed in claim 1, wherein the extraction column is a packed column having from 2 to 10 theoretical plates.

9. A process for the preparation of a monoester of (meth)acrylic acid with a $C_4$–$C_6$-alkanediol by esterification of (meth)acrylic acid with this alkanediol in the presence of an acidic esterification catalyst with removal of the resulting water by azeotropic distillation with an entraining agent, separation of the product mixture by extraction with an extracting agent 1 in an organic solution containing the diester formed as by-product and an aqueous solution containing the alkanediol used and (meth)acrylic monoester and subsequent separation of the (meth)acrylic monoester by extraction from the aqueous solution containing the alkanediol used and (meth)acrylic monoester with an extracting agent 2 and subsequent separation of extracting agent 2 and (meth)acrylic monoester, in which the extracting agent 1 and the azeotropic entraining agent are chemically identical and the organic solution containing the diester formed as a byproduct (extract 1) is recycled to the esterification, wherein the product mixture is added continuously to the middle section of an extraction column and in addition water and the organic extracting agent 1 are passed continuously countercurrent in the extraction column.

10. A process as claimed in claim 9, which is a process for the preparation of 1,4-butanediol monoacrylate.

11. A process as claimed in claim 1, wherein the extraction column is a packed column having 4 to 6 theoretical plates.

* * * * *